(12) United States Patent
Peppas et al.

(10) Patent No.: US 10,086,091 B2
(45) Date of Patent: Oct. 2, 2018

(54) METHOD OF PREPARATION OF BIODEGRADABLE NANOPARTICLES WITH RECOGNITION CHARACTERISTICS

(71) Applicant: Board of Regents, The University of Texas System, Austin, TX (US)

(72) Inventors: Nicholas Peppas, Austin, TX (US); Heidi Culver, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 15/080,165

(22) Filed: Mar. 24, 2016

(65) Prior Publication Data

US 2016/0199516 A1 Jul. 14, 2016

Related U.S. Application Data

(63) Continuation of application No. PCT/US2014/057812, filed on Sep. 26, 2014.

(60) Provisional application No. 61/883,630, filed on Sep. 27, 2013.

(51) Int. Cl.
*A61K 49/00* (2006.01)
*C08F 283/06* (2006.01)
*A61K 9/51* (2006.01)

(52) U.S. Cl.
CPC ...... *A61K 49/0093* (2013.01); *A61K 49/0054* (2013.01); *C08F 283/065* (2013.01); *A61K 9/5146* (2013.01); *A61K 9/5153* (2013.01)

(58) Field of Classification Search
None
See application file for complete search history.

(56) References Cited

FOREIGN PATENT DOCUMENTS

| EP | 1591467 | * | 9/2003 | .......... C08G 65/359 |
| WO | WO2012154332 | * | 11/2012 | .............. C09K 8/60 |

OTHER PUBLICATIONS

Fu et al (Enhanced Lysozyme Imprinting Over Nanoparticles Functionalized with Carboxyl Groups for Noncovalent Template Sorption. Anal. Chem., 2011, 83 (4), pp. 1431-1436).*
Ning et al (Versatile fabrication of water-dispersible nanoparticle—amphiphilic copolymer composite microspheres with specific functionalities. J. Mater. Chem., 2011, 21, 6837-6843).*
Chawla et al (Biodegradable poly(o-caprolactone) nanoparticles for tumor-targeted delivery of tamoxifen. Int J Pharm. Dec. 5, 2002;249(1-2):127-38).*
Ryu et al (Preparation of Core-shell Type Nanoparticles of Poly(e-caprolactone)/Poly(ethylene glycol)/Poly(e-caprolactone) Triblock Copolymers. Bull. Korean Chem. Soc. 2001, vol. 22, No. 5 p. 467-475).*

* cited by examiner

*Primary Examiner* — Jake M Vu
(74) *Attorney, Agent, or Firm* — Reed Smith LLP; Robert R. Riddle; Matthew S. Gibson

(57) ABSTRACT

The present disclosure relates to a novel type of recognitive biodegradable nanoparticles and their preparations. In particular, the present disclosure relates to combinations of MIPs and biodegradable nanoparticles.

3 Claims, 8 Drawing Sheets
(3 of 8 Drawing Sheet(s) Filed in Color)

| Substrate | Vinyl stabilizer | Functional monomers |
|---|---|---|

*Poly(ε-caprolactone)*  *PMAO-g-PEGMA*  DMAEMA (positive)
MAA (negative)
- Biodegradable  • Polyamphiphile  Aam (neutral)
- Easy encapsulation  • Negatively charged  MBA (crosslinker)
- Inexpensive  • Pendant vinyl groups

METHOD OF PREPARATION OF BIODEGRADABLE NANOPARTICLES WITH RECOGNITION CHARACTERISTICS

CROSS-REFERENCE TO RELATED APPLICATIONS

This application is a continuation of International Application No. PCT/US14/57812, filed Sep. 26, 2014, which claims the benefit of U.S. Provisional Application Ser. No. 61/883,630 filed on Sep. 27, 2013, the entirety of which is incorporated by reference.

STATEMENT OF GOVERNMENT INTEREST

This invention was made with support under Award No. DGE-1110007, awarded by National Science Foundation. The U.S. government has certain rights in the invention

BACKGROUND

Molecularly imprinted polymers (MIPs) are polymers that can selectively recognize target molecules. This is achieved by allowing the target molecule, referred to as the template, to pre-assemble with certain monomers that have functional groups that can form non-covalent interactions with functional groups in the structure of the template. For example, functional monomers with positively charged functional groups can form electrostatic interactions with negatively charged side chains of amino acid residues on the surface of a protein. After pre-assembly, free radical polymerization is initiated and a polymer network with cavities that are complementary to the template in both shape and functionality is formed (FIG. 1). After thorough washing to remove the template from the polymer, the polymer can then selectively rebind to the template, similar to how an antibody would recognize its antigen. These polymers are used in a number of medical applications, including diagnostics, microsensors, biosensors, drug discovery, controlled release of drugs in response to interaction with the target molecule, and accelerated clearance of undesirable molecules from the body.

In recent years, many investigators have had a significant interest in discovering biomarkers that can be used for diagnostic tests. Biomarkers are indicators of the physiological state and change during a disease's progression. They reflect changes in the active genes of a cell and the products of these genes, such as proteins. Being able to sensitively detect these molecules at an early stage of a disease or before a recurrent flare could lead to more favorable treatment options and better prognoses. However, it has been a challenge to achieve this early detection and thus widespread use of diagnostic screening tests in the clinic has not yet been seen for a number of reasons. The current tests lack specificity and sensitivity, which are measures of how well the test can discern healthy people from people with the disease. Furthermore, these tests use proteins, specifically antibodies and enzymes, which are expensive and have poor shelf life. It will be necessary to develop a highly cost-effective diagnostic test, especially for regular, systematic mass screening that would be needed for them to be effective. Another disadvantage of current diagnostic techniques, such as biopsies, is that they can be invasive and uncomfortable for the patient. An alternative to this invasive technique is to use in vivo optical imaging techniques to identify biomarker levels and localization. These techniques involve the use of a recognitive material, typically an antibody, and a contrast reagent such a near infrared dye or gadolinium. These approaches, however, are limited due to, among other things, toxicity from injecting foreign antibodies and contrast agents into the body.

SUMMARY

The present disclosure generally relates to a novel type of recognitive biodegradable nanoparticles and their preparations. In particular, the present disclosure relates to combinations of MIPs and biodegradable nanoparticles.

Molecular imprinted polymer nanoparticles (MIPNPs) may help overcome the challenges described above. MIPNPs have a lower cost of production compared to the antibodies and are easier to scale up than natural materials. Because they are synthetically produced, they can be optimized to have high affinity and selectivity. They also may serve as a non-invasive tool and avoid the potential immunologic response that comes with the use of natural materials in the body.

One aspect of the present disclosure is directed to a composition comprising: an outer shell having at least one binding cavity specific for a target molecule; and a biodegradable inner core substantially free of the binding cavity.

Another aspect of the present disclosure is directed to a novel polymer platform, poly(maleic anhydride-alt-1-octadecene)-g-poly(ethylene glycol) methacrylate (PMAO-g-PEGMA).

Another aspect of the present disclosure is directed to a composition comprising a hydrophobic particle and an amphiphilic polymer.

These nanoparticles can be used for in vivo diagnostics by accurately detecting variations in the concentration and localization of a certain protein or other biomacromolecule that is overexpressed in a disease, such as cancer. The use of biodegradable nanoparticles is advantageous because the body can easily break it down into non-toxic components if used for in vivo diagnostic or therapeutic applications. The compositions disclosed in the present disclosure can also be used in the consumer and cosmetic field.

Another aspect of the present disclosure is directed to a method comprising:
  a) dissolving hydrophobic polymers or particles in a solvent;
  b) dissolving amphiphilic polymers in a aqueous solution;
  c) mixing the hydrophobic polymer or particle solution with the aqueous solution of amphiphilic polymers.

Such process can be easily scaled up for industry. Additionally, during this process, active agents, such as fluorophores, therapeutic agents or other hydrophobic agents can be easily encapsulated in the particle core.

The features and advantages of the present disclosure will be readily apparent to those skilled in the art. While numerous changes may be made by those skilled in the art, such changes are within the spirit of the invention.

DRAWINGS

The patent or application file contains at least one drawing executed in color. Copies of this patent or patent application publication with color drawings will be provided by the office upon request and payment of the necessary fee.

The patent or application file contains at least one drawing executed in color. Copies of this patent or patent application publication with color drawing(s) will be provided by the Office upon request and payment of the necessary fee.

A more complete understanding of this disclosure may be acquired by referring to the following description taken in combination with the accompanying figures in which:

FIG. 1 shows a general procedure for molecular imprinting. (Left) A template molecule is incubated with a set of functional monomers and crosslinking monomers to preassemble. (Center) After free radical polymerization, a network is created that has the template still inside the pores. (Right) The template molecule is washed out, leaving cavities that are complementary to the template in both shape and functionality.

Figure 5:
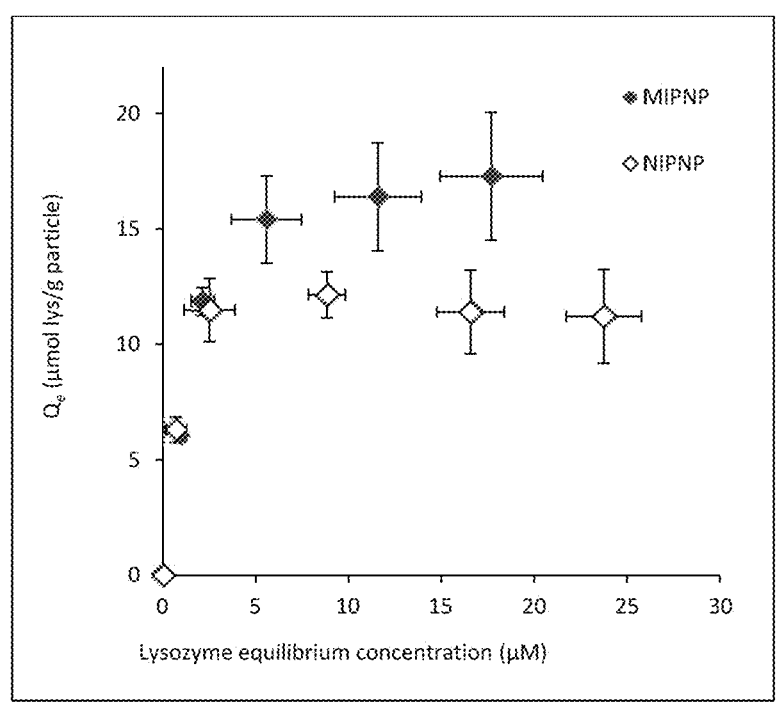

FIG. 5 shows results from the batch rebinding studies of MIPNPs and non-imprinted nanoparticles (NIPNPs). Batch rebinding studies are a common way to compare MIPs and are done by incubating a known mass of the MIPNPs with varying concentrations of template until binding equilibrium is reached. By measuring the amount of template left in the supernatant, the amount that adsorbed to the nanoparticles can be calculated and the data can be fit to adsorption isotherms, such as Langmuir or Freundlich, in order to extract binding parameters. Data represent values from triplicate experiments and error bars represent ±1 standard deviation.

Figure 6:
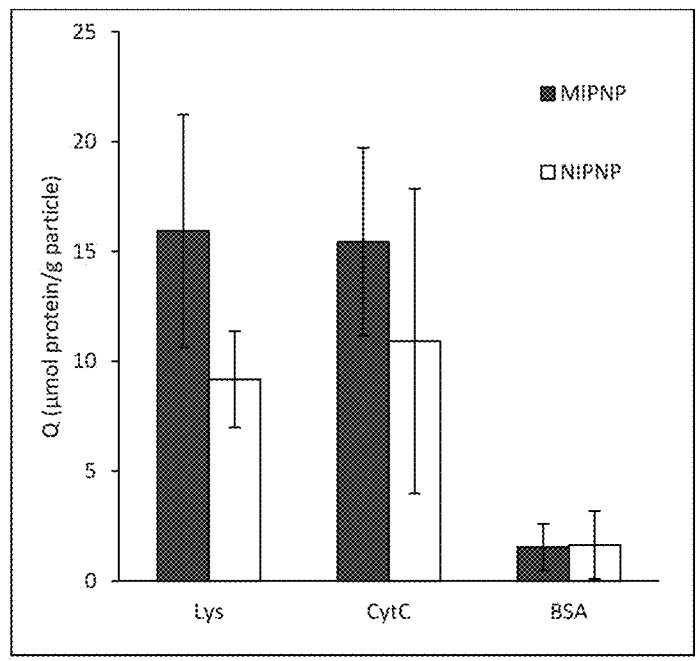

FIG. 6 shows rebinding capacity for lysozyme and two other proteins when incubated individually in simple buffers. Cytochrome c (Cyt c) and bovine serum albumin (BSA) were the proteins selected for comparison. Cyt c is a structural analog to lysozyme, having similar a molecular weight and isoelectric point, making it a potential competitor to lysozyme in more complex media. BSA is a much larger protein with a low isoelectric point and thus was expected to have low binding to the MIPNPs except for non-specific adsorption. The results show that the MIPNPs have the highest binding affinity for lysozyme, followed closely by Cyt c and very low adsorption of BSA, demonstrating their specificity for lysozyme. Data represent values from triplicate experiments and error bars represent ±1 standard deviation.

Figure 7:
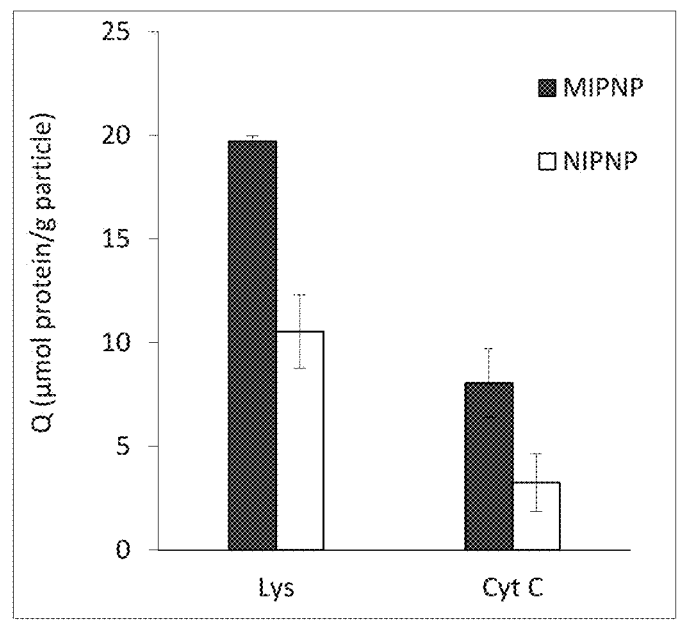

FIG. 7 shows results from competitive rebinding study to test adsorption specificity. Lysozyme and cytochrome c were incubated together to see if cytochrome c would interfere or compete with lysozyme binding. Data represent values from duplicate experiments and error bars represent ±1 standard deviation.

Figure 8:
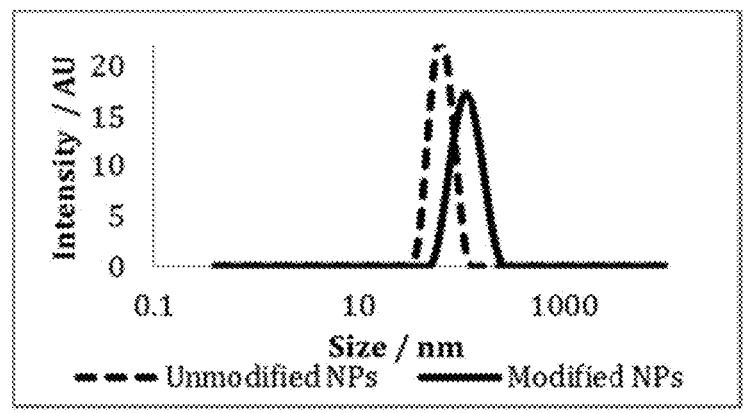
Figure 9:
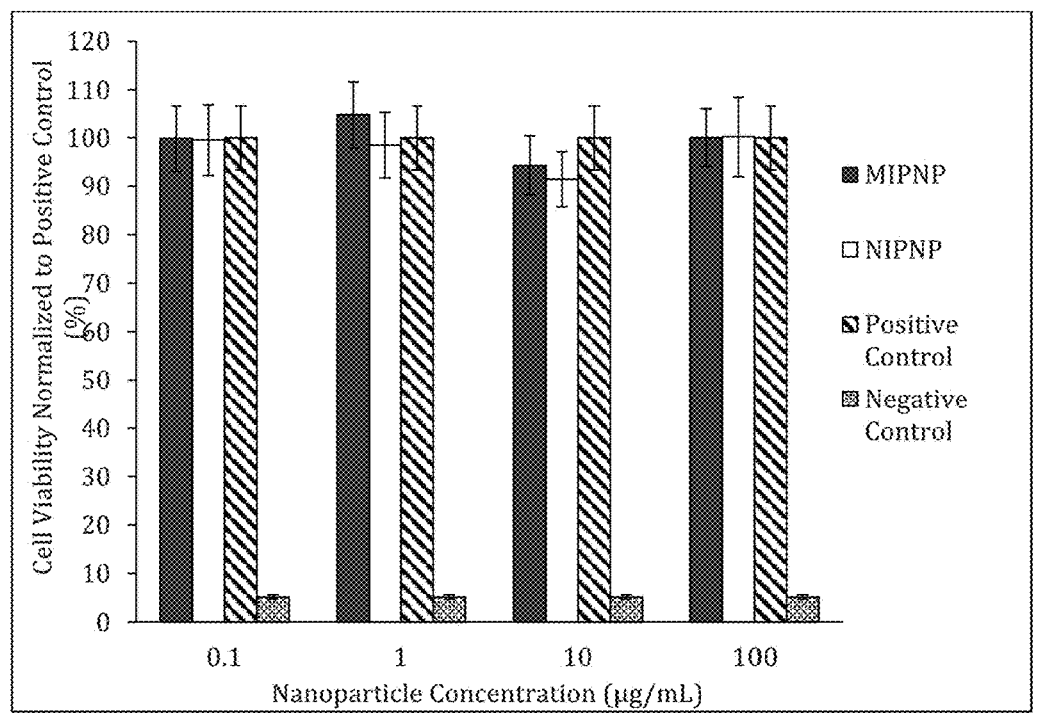

FIG. 8 shows dynamic light scattering results showing increase in polystyrene nanoparticle size when coated with PMAO-g-PEGMA FIG. 9 shows results of cytotoxicity studies. Raw macrophages were plated in a 96-well plate and then incubated with four concentrations (0.1, 1, 10, 100 μg/mL) of imprinted particles or non-imprinted particles (n=8 for each concentration), DMEM (positive control, n=8) or 1.5% v/v bleach in DMEM (negative control, n=8). Cell viability was determined using an MTS assay.

Figure 10:
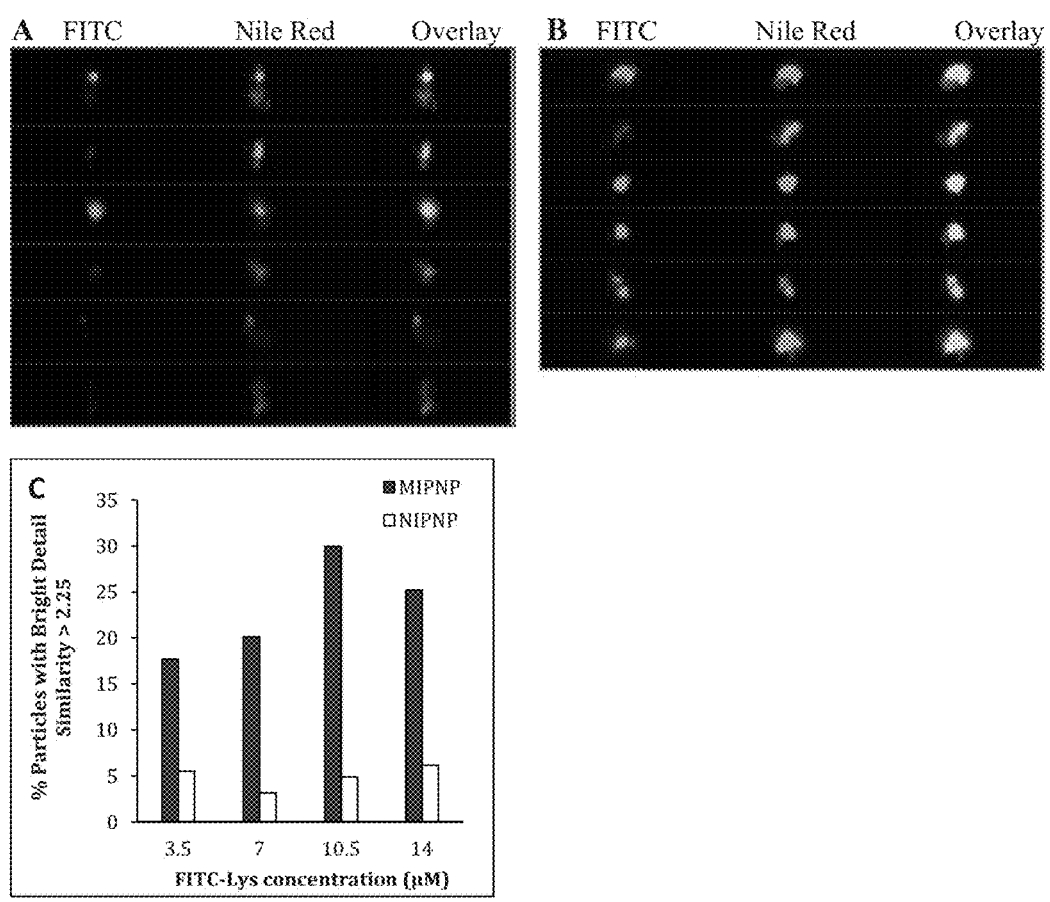

FIG. 10 shows results from imaging flow cytometry followed by co-localization analysis. (A) Representative images of NIPs; (B) Representative images of MIPs; and (C) Results from co-localization analysis.

Figure 11:
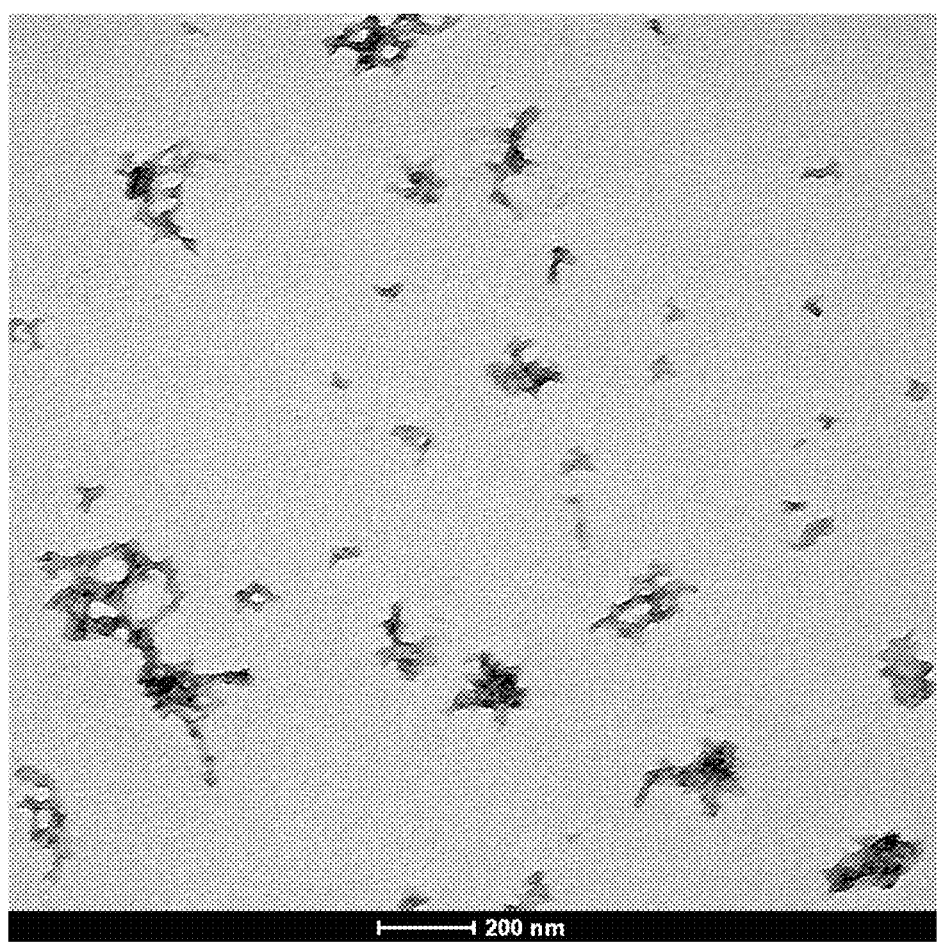

FIG. 11 shows representative TEM image of particles after washing the particles with 10% acetic acid to remove the lysozyme template. Particles were stained with 2% uranyl acetate.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as defined by the appended claims.

DESCRIPTION

The present disclosure generally relates to a novel type of recognitive biodegradable nanoparticles and their preparations. In particular, the present disclosure relates to combinations of MIPs and biodegradable nanoparticles.

The present disclosure provides, according to certain embodiments, compositions comprising an outer shell having at least one binding cavity specific for a target molecule (i.e., a molecularly imprinted polymer) disposed around a biodegradable inner core.

In general, the biodegradable inner core (also referred to as the "substrate") should be formed from a material that is biodegradable (e.g., bioresorbable) and biocompatible. Such cores are better able to avoid cytotoxicity, as is seen with inorganic materials like silicas. The biodegradable inner core may be a nanoparticle and may have a surface that is at least partially hydrophobic. For example, the biodegradable inner core may be a poly(ε-caprolactone) (PCL) nanoparticle. In certain embodiments, a therapeutic agent may be disposed within or encapsulated by the biodegradable inner core.

In certain embodiments, biodegradation of the biodegradable inner core can be controlled to occur after the complete recognition of the target molecule.

As noted above, the outer shell has at least one binding cavity specific for a target molecule (i.e., a molecularly imprinted polymer or MIP). In certain embodiments, the outer shell comprises at least one amphiphilic polymer.

In certain embodiments, the outer shell is surface imprinted to a target molecule. Such surface imprinted MIPs have a structure in which imprinted binding cavities are localized toward an outer surface of the MIP. MIPs are formed from one or more functional monomers and optionally one or more crosslinkers.

MIPs suitable for use in the compositions and methods of the present disclosure include polymers that can selectively sense, for example, through recognition, detection and binding, a target molecule which was present when the MIP was formed and later removed. This target molecule may be any of a variety of compounds of interest which is capable of being selectively recognized by the MIP Examples of suitable MIPs may be found in U.S. Pat. Nos. 7,771,732, 8,304,247, as well as U.S. Patent Application Publication No. 2007/0071712 published Mar. 29, 2007, PCT Application Publication No. WO 2008/039920 published Apr. 3, 2008, U.S. Patent Application Publication No. 2007/0190084 published Aug. 16, 2007, and PCT Application Serial Number PCT/US2007/83362 filed Nov. 1, 2007, the entire disclosures of which are incorporated by reference. Some advantages of certain MIPs may include their physical and chemical stability, low cost of fabrication, and their ability to be customizable to many applications.

In certain embodiments, the target molecule may be a biomolecule, including, but are not limited to, a protein (e.g., lysozyme or other biomarkers listed in Table 1), a polypeptide, a peptide, a carbohydrate (such as a monosaccharide, an oligosaccharide, or a polysaccharide), a glycoprotein, a proteoglycan, or any other suitable biological molecule. In certain embodiments, the target molecule may be a medically relevant compound, including, but not limited to, glucose, serotonin, C-reactive protein, a virus, or a cell. In certain embodiments, the molecular decoy may be attached to a second compound, among other things, to allow easier formation of the MIP or detection of this second compound than if the second compound itself were used as a target molecule. MIPs may detect target molecules of a variety of sizes.

TABLE 1

Examples of Some Protein Biomarkers

| CANCER | |
|---|---|
| Leukemia | Lysozyme |
| Breast, lung, prostate | Osteopontin |
| INFLAMMATORY DISEASES | |
| Multiple sclerosis | Osteopontin |
| Meningitis | Lysozyme |
| Rheumatoid arthritis | Anti-cyclic citrullinated peptide |
| CARDIOVASCULAR DISEASES | |
| Atherosclerosis | C-reactive protein, Fetuin A |
| Coronary artery disease | Hyaluronidase |

MIPs may be synthesized by free radical polymerization of any monomer and crosslinking agent able to form an MIP having at least one binding cavity for the target molecule. To form the MIP, the monomer and crosslinking agent may be brought together in the presence of the target molecule. After polymerization, the target molecule is removed without destroying the MIP. Suitable polymerization methods may include, but are not limited to, free radical polymerization, anionic polymerization, cationic polymerization, stereospecific (Ziegler Natta) polymerization, or atom transfer radical polymerization (ATRP). The MIP retains a binding site able to bind and thus sense the target molecule. The binding site typically exhibits specificity to the target molecule. In certain embodiments, the binding site may be highly specific such that it can distinguish between two very similar target molecules, or polypeptides differing by only one amino acid. In certain embodiments, the specificity of the MIP may be such that it is biomimetic, that is, it mimics the recognition abilities of a biological molecule or pathway, such as an antibody. In certain embodiments, MIPs may be made and/or used in the form of hydrogel networks, gels, or polymers.

Suitable monomers to form MIPs useful in the compositions and methods of the present disclosure may include, but are not limited to, acrylic acid, methacrylic acid, ethacrylic acid, propacrylic acid, various acrylates, methacrylates, and acrylamides. Derivatives of these compounds may also be suitable. The term "derivative," as used herein, includes any compound that is made from one of the listed compounds, for example, by replacing one atom in the listed compound with another atom or group of atoms, rearranging two or more atoms in the listed compound, ionizing one of the listed compounds, or creating a salt of one of the listed compounds. In certain embodiments, the MIPs useful in the compositions and methods of the present disclosure may be formed from more than one monomer and thus may be a copolymer. The term "copolymer," as used herein, is not limited to polymers comprising two types of monomeric units, but includes any combination of monomeric units, e.g., terpolymers, tetrapolymers, and the like.

Suitable crosslinking agents include, but are not limited to, ethylene glycol dimethacrylate, diethylene glycol dimethacrylate, triethylene glycol dimethacrylate, tetraethylene glycol dimethacrylate, poly(ethylene glycol dimethacrylate), bisacrylamides and divinyl benzene. Derivatives of these compounds may also be suitable. These crosslinking agents may contain between 5 and 100 units, specifically between about 5 and 25 units and more specifically between about 5 and 10 units. Suitable crosslinking agents can also be biodegradable.

In a specific embodiment, the MIP is formed from used dimethylaminoethyl methacrylate, methacrylic acid, acrylamide, and methylene bisacrylamide as the crosslinker.

Figures 1, 2:
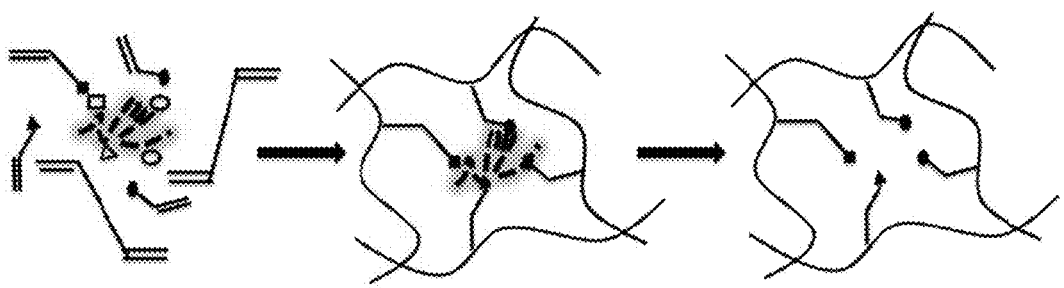
FIG. 2 shows components of one type of MIPNP disclosed in the present disclosure.

FIG. 2 illustrates one type of MIPNP disclosed in the present disclosure, with binding cavities specific for lysozyme. For example, the substrate (the inner core) for imprinting can be a PCL nanoparticle. The nanoparticles were stabilized by a vinyl stabilizer, e.g., PMAO-g-PEGMA. Both positively (2-(dimethylamino)ethyl methacryate) and negatively (methacrylic acid) charged functional monomers were used in this system because the active binding sites of lysozyme have both positively and negatively charged amino acid residues. Acrylamide and N,N'-methylene bisacrylamide were also used to help control pore size. However, other vinyl monomers can be selected and varied to optimize the system for other template molecules (target molecules).

Additionally, the MIPNPs of the present disclosure showed more absorption capacity and more uniform binding cavities than the non-imprinted nanoparticles (NIPNPs). The relevant absorption isotherm equations and variables are listed in Table 2.

TABLE 2

Adsorption isotherm equations and variables

| | Equation | Variables |
|---|---|---|
| Langmuir isotherm | $Q = \dfrac{Q_{max} K C_e}{1 + K C_e}$ | $K = \dfrac{[LR]}{[L][R]}$ = equilibrium constant |
| | | $Q = \dfrac{[C_o - C_e]V}{m}$ = amount of template adsorbed (mg/g) |
| | | $Q_{max}$ = adsorption capacity |
| | | $C_e$ = equilibrium template concentration |

TABLE 2-continued

Adsorption isotherm equations and variables

| | Equation | Variables |
|---|---|---|
| Freundlich isotherm | $B = aF^m$ | $B$ = amount of bound template (i.e., Q)<br>$a$ = measure of capacity and affinity<br>$F$ = amount of free template (i.e. $C_e$)<br>$m$ = heterogeneity index (ranges from 0 (heterogeneous) to 1 (homogeneous)) |

In one example, batch rebinding studies were used to quantify adsorption capacity of lysozyme to the imprinted particles. In these studies, a constant mass of polymer particles was incubated with varying concentrations of lysozyme for 60 minutes in order to allow re-binding to occur and equilibrium to be reached. Then, particles were centrifuged and the amount of lysozyme that did not bind to the nanoparticles was quantified by measuring the absorbance of the supernatant at 280 nm. Non-imprinted polymer nanoparticles (NIPNPs) were treated identically to the imprinted nanoparticles (MIPNPs) except lysozyme was excluded during polymerization. As shown in FIG. 5, equilibrium concentrations of free lysozyme ($C_e$) were plotted against the adsorption capacity of lysozyme per gram of particle ($Q_e$) as calculated by $$Q_e = \frac{(C_o - C_e)V}{m}$$

where $C_o$ is the initial concentration of lysozyme, $C_e$ is the equilibrium concentration of free lysozyme, V is the volume of buffer used during rebinding and m is the mass of particles. According to the Langmuir isotherm fits (not shown), the MIPNPs had an adsorption capacity of 19.0 µmol lysozyme/g nanoparticle and the NIPNPs only had an adsorption capacity of 12.2 µmol lysozyme/g nanoparticle. This is an imprinting factor of 1.55, meaning that the MIPNPs are capable of binding 55% more lysozyme than the NIPNPs.

Furthermore, the MIPNPs of the present disclosure showed rebinding specificity over the target molecule than the NIPNPs. The MIPNPs and NIPNPs were incubated separately with three different proteins, lysozyme (the target molecule), Cytochrome C, and bovine serum albumin (BSA), in the rebinding tests. Cytochrome C was selected due to the fact that it has a similar molecular weight, size, and isoelectric point to lysozyme. BSA is much larger and has a much lower isoelectric point than lysozyme but was used to determine non-specific adsorption. As shown in FIG. 6, these results show that the imprinted particles do have the highest binding affinity for lysozyme, followed closely by cytochrome C and low adsorption of BSA. These results demonstrate the size and isoelectric point specificity of the lysozyme MIPNPs, but the formulation may need further optimization to improve the specificity of the MIPNPs towards lysozyme over proteins with similar properties.

In another example, competitive rebinding studies were performed to test adsorption specificity. The particles were incubated with both lysozyme and cytochrome C in the same tube in order to see if cytochrome C would interfere or compete with lysozyme binding to the MIPNPs. The equilibrium concentrations of both proteins were quantified in two ways: absorbance measurements at both 280 nm and 410 nm (wavelength at which only cytochrome C absorbs light) and reverse-phase HPLC. As shown in FIG. 7, both methods of protein quantitation produced similar results, demonstrating specificity of the MIPs towards lysozyme over cytochrome C when incubated together.

Another aspect of the present disclosure is directed to a novel polymer platform, poly(maleic anhydride-alt-1-octadecene)-g-poly(ethylene glycol) methacrylate (PMAO-g-PEGMA). Accordingly, the present disclosure also provides, according to certain embodiments compositions comprising PMAO-g-PEGMA disposed on a surface. Examples of suitable surfaces include, but are not limited to, PCL nanoparticles, quantum dots, poly(lactic-co-glycolic acid) (PLGA) nanoparticles, and other clinically relevant nanoparticles.

PMAO-g-PEGMA may be used to modify the surfaces, such as hydrophobic particle surfaces, for surface imprinting. It is an amphiphilic brush polymer. In each repeat unit, there is a hydrophobic component (octadecene), a hydrophilic group (PEGMA), the vinyl group at the end of the PEGMA, and a carboxyl group, which will be negatively charged and help localize templates at the surface of the nanoparticles via electrostatic interactions.

PMAO-g-PEGMA synthesis is shown in Scheme 1. Briefly, Poly(ethylene glycol) methacrylate (PEGDMA) was grafted onto poly(maleic anhydride-alt-1-octadecene) (PMAO) via ring opening of the maleic anhydride. The chemical structures of the polymer reagents and the resultant polymer, PMAO-g-PEGMA, were verified by ¹H-NMR spectroscopy.

Scheme 1. Reaction for synthesizing PMAO-g-PEGMA.

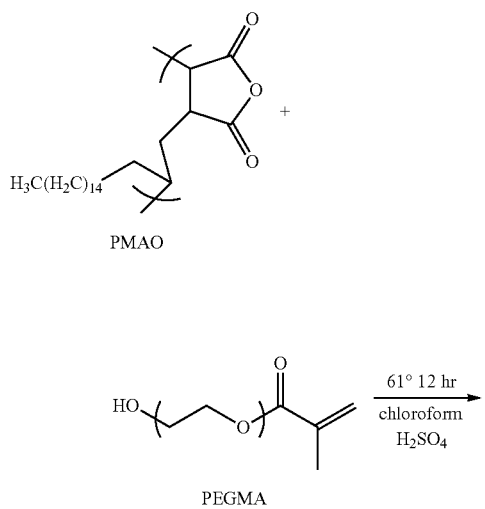

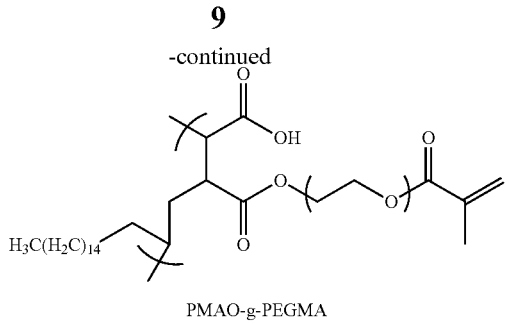

PMAO-g-PEGMA

In one example, solvent displacement was used to encapsulate polystyrene nanoparticles in PMAO-g-PEGMA. Size and charge of the modified and unmodified polystyrene nanoparticles were compared using dynamic light scattering and zeta potential measurements, respectively. (FIG. 8.)

As noted previously, the compositions of the present disclosure may further comprise an active agent. Examples of an active agent include, but are not limited to, a fluorophore, a therapeutic agent (e.g., a drug and/or a pharmaceutically active ingredient), or a hydrophobic agent.

The compositions of the present disclosure may also be used in consumer and cosmetic field to deliver any suitable active agents.

Another aspect of the present disclosure is directed to a method comprising:

a) dissolving hydrophobic polymers or particles in a solvent;
b) dissolving amphiphilic polymers in a aqueous solution;
c) mixing the hydrophobic polymer or particle solution with the aqueous solution of amphiphilic polymers.

Figure 3:
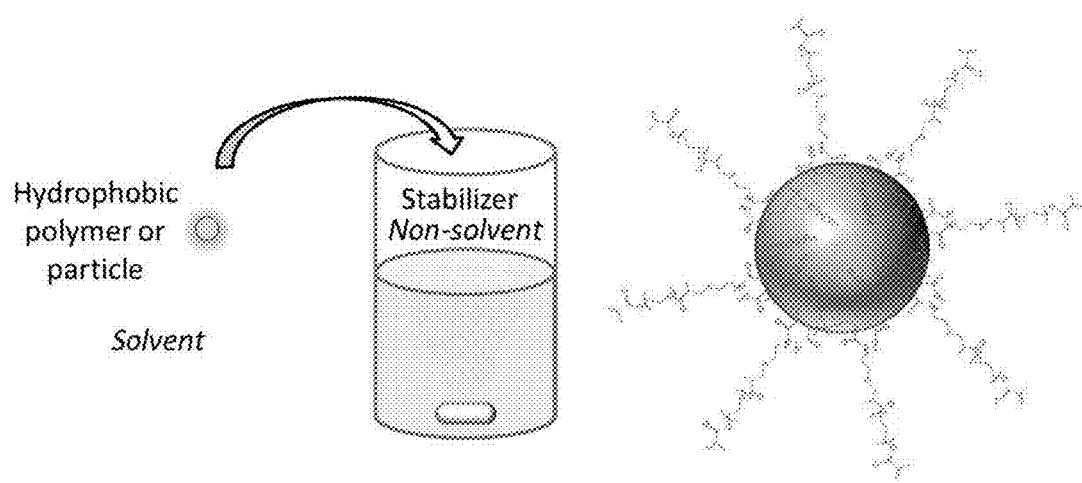
FIG. 3 shows solvent displacement method of forming PMAO-g-PEGMA stabilized PCL nanoparticles.

For Example, as shown in FIG. 3, PMAO-g-PEGMA stabilized PCL nanoparticles can be formed using the solvent displacement method. PCL was dissolved in acetone and then added to an aqueous solution of the PMAO-g-PEGMA. The hydrophobic nature of PCL caused it to collapse and aggregate with itself in the presence of water, a non-solvent for PCL. The hydrophobic portions of PMAO-g-PEGMA adsorb to the PCL nanoparticles and the hydrophilic branches remain reaching into the water, forming a stable, aqueous dispersion of PCL nanoparticles.

In certain embodiments, the method further comprising d) freeze drying the dispersion obtained in c).

In certain embodiments, the method further comprising e) re-suspending the solid obtained in d).

In another embodiment, the solution of nanoparticles is added to the aqueous solution of amphiphilic polymers.

In certain embodiments, the amphiphilic polymers are vinyl stabilizers. In a further embodiment, the amphiphilic polymers are PMAO-g-PEGMA. FIG. 2 illustrates this embodiment.

In another embodiment, the hydrophobic particles are biodegradable.

In certain embodiments, the hydrophobic particles are nanoparticles. In a further embodiment, the hydrophobic particles are PCL nanoparticles.

Figure 4:
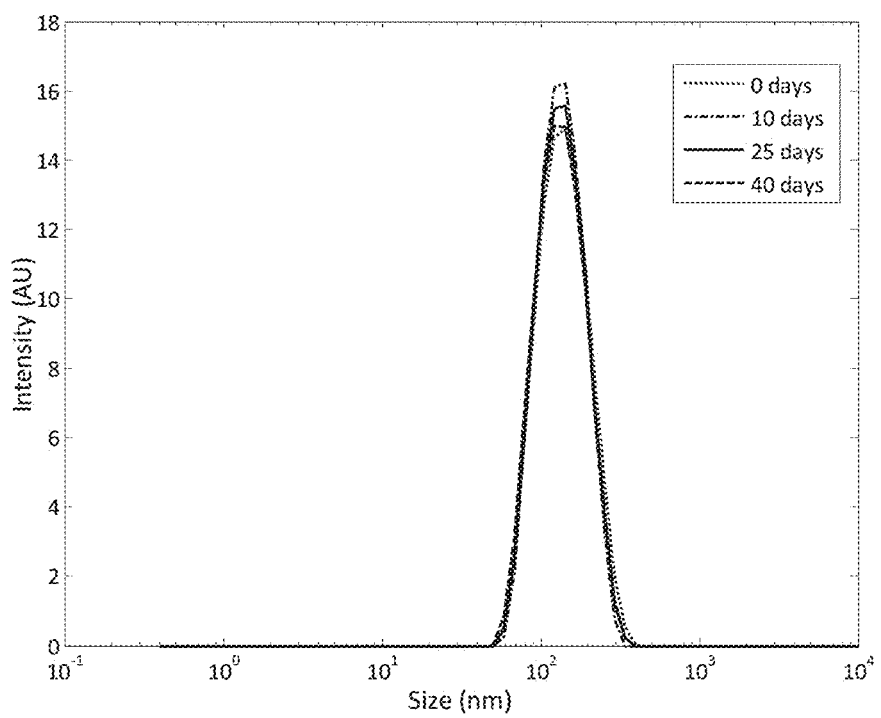
FIG. 4 shows dynamic light scattering results that demonstrate the stability and homogeneity of the PMAO-g-PEGMA stabilized PCL nanoparticles.

As shown in FIG. 4, dynamic light scattering results showed the stability and homogeneity of the PMAO-g-PEGMA stabilized PCL nanoparticles. The particles remained stable in water for over 40 days, with the PDI never reaching above 0.11. The average hydrodynamic radius of the particles was 63.7 with a zeta potential of −68.2 mV. The negative zeta potential was expected due to the presence of the carboxyl groups along the PMAO-g-PEGMA backbone.

In certain embodiments, an active agent can be added to the process to be encapsulated in the particles.

In another example, cytotoxicity studies were performed in which cell viability was assessed using an MTS assay. The results are shown in FIG. 9.

In another example, imaging flow cytometry followed by co-localization analysis demonstrated that at all concentrations of FITC-lysozyme tested, there were more imprinted nanoparticles with a bright detail similarity score>2.25. Representative images of NIPs and of MIPs are shown in FIG. 10(A) and FIG. 10(B), respectively. The results from co-localization analysis are shown in FIG. 10(C). The brightness similarity score is a measure of how similar individual pixel intensities are in the two channels. A score above 2.25 corresponds to a Pearson correlation coefficient greater than 0.8 and suggests co-localization of the two fluorophores.

In another example, TEM was used to image MINPs after washing with 10% acetic acid to remove the lysozyme template. The particles were stained with 2% uranyl acetate. Representative particles are shown in FIG. 11, which show that after imprinting and washing particles have an irregular morphology.

Terms such as "a", "an" and "the" are not intended to refer to only a singular entity, but include the general class of which a specific example may be used for illustration. The terminology herein is used to describe specific embodiments of the disclosure, but their usage does not delimit the disclosure, except as outlined in the claims.

To facilitate a better understanding of the present disclosure, the following examples of certain aspects of some embodiments are given. In no way should the following examples be read to limit, or define, the entire scope of the invention.

What is claimed is:

1. A composition comprising an outer shell having at least one binding cavity specific for a target molecule and wherein the outer shell comprises poly(maleic anhydride-alt-1-octadecene)-g-poly(ethylene glycol) methacrylate (PMAO-g-PEGMA); and a biodegradable inner core comprising poly(ε-caprolactone) (PCL) and substantially free of the binding cavity.

2. The composition of claim 1, further comprising an active agent.

3. The composition of claim 2, wherein the active agent is a fluorophore, a therapeutic agent, or a hydrophobic agent.

* * * * *